(12) United States Patent
Wang (10) Patent No.: US 12,011,204 B2
(45) Date of Patent: Jun. 18, 2024

(54) FLOW RATE CONTROL FOR A COOLED MEDICAL PROBE ASSEMBLY

(71) Applicant: Avent, Inc., Alpharetta, GA (US)

(72) Inventor: Ruoya Wang, Decatur, GA (US)

(73) Assignee: Avent, Inc., Alpharetta, GA (US)

( * ) Notice: Subject to any disclaimer, the term of this patent is extended or adjusted under 35 U.S.C. 154(b) by 446 days.

(21) Appl. No.: 17/391,448

(22) Filed: Aug. 2, 2021

(65) Prior Publication Data

US 2022/0015814 A1   Jan. 20, 2022

Related U.S. Application Data (63) Continuation of application No. 16/227,610, filed on Dec. 20, 2018, now Pat. No. 11,076,904.

(51) Int. Cl.
*A61B 18/00* (2006.01)
*A61B 17/00* (2006.01)

(52) U.S. Cl.
CPC ...... *A61B 18/00* (2013.01); *A61B 2017/0023* (2013.01); *A61B 2018/00023* (2013.01); *A61B 2018/0044* (2013.01); *A61B 2018/00642* (2013.01); *A61B 2018/00744* (2013.01); *A61B 2018/00863* (2013.01)

(58) Field of Classification Search
CPC ............ A61B 18/00; A61B 2017/0023; A61B 2018/00011; A61B 2018/00023; A61B 2018/0044; A61B 2018/00642; A61B 2018/00744; A61B 2018/00863
USPC .......................................................... 606/1
See application file for complete search history.

(56) References Cited

U.S. PATENT DOCUMENTS

| 6,063,051 A | 5/2000 | Stern | |
|---|---|---|---|
| 2003/0236489 A1* | 12/2003 | Jacobson | A61M 5/172 604/67 |
| 2005/0177211 A1* | 8/2005 | Leung | A61B 18/148 607/101 |

(Continued)

FOREIGN PATENT DOCUMENTS

EP   3412237 A1   12/2018

OTHER PUBLICATIONS

Search Report and Written Opinion for PCT/US2019/066691, dated Apr. 6, 2020, 13 pages.

*Primary Examiner* — Erin M Pieteski
(74) *Attorney, Agent, or Firm* — Meunier Carlin & Curfman LLC (57) ABSTRACT

Cooling systems for medical probe assemblies are provided. For example, a cooling system comprises a pump assembly including a control unit having a controller, a motor, and a pump head driven by the motor; a fluid reservoir; a lumen for delivering a cooling fluid to the medical probe assembly distal end; tubing extending through the pump head for conveying the cooling fluid from the fluid reservoir to the lumen; and a flow sensor for sensing the cooling fluid flow rate. The pump head is disposed between the fluid reservoir and the medical probe assembly to pump the cooling fluid from the fluid reservoir to the lumen. The flow sensor is disposed between the pump head and the medical probe assembly to sense the cooling fluid flow rate. Methods for controlling fluid flow rate through a cooling circuit and systems for using a plurality of medical probe assemblies also are provided.

11 Claims, 5 Drawing Sheets

(56) References Cited

U.S. PATENT DOCUMENTS

| | | | |
|---|---|---|---|
| 2013/0177455 A1* | 7/2013 | Kamen | G16H 20/17 |
| | | | 417/313 |
| 2016/0018347 A1 | 1/2016 | Drbal et al. | |
| 2016/0206279 A1 | 7/2016 | Arts et al. | |
| 2017/0156783 A1* | 6/2017 | McKernon | A61B 18/1206 |

\* cited by examiner

FLOW RATE CONTROL FOR A COOLED MEDICAL PROBE ASSEMBLY

FIELD

The present subject matter relates generally to medical probe assemblies and, more particularly, to methods and systems for controlling the flow rate of a cooling fluid to the medical probe assembly.

BACKGROUND

Lower back injuries and chronic joint pain are major health problems resulting not only in debilitating conditions for the patient, but also in the consumption of a large proportion of funds allocated for health care, social assistance and disability programs. In the lower back, disc abnormalities and pain may result from trauma, repetitive use in the workplace, metabolic disorders, inherited proclivity, and/or aging. The existence of adjacent nerve structures and innervation of the disc are very important issues in respect to patient treatment for back pain. In joints, osteoarthritis is the most common form of arthritis pain and occurs when the protective cartilage on the ends of bones wears down over time.

A minimally invasive technique of delivering high-frequency electrical current has been shown to relieve localized pain in many patients. Generally, the high-frequency current used for such procedures is in the radiofrequency (RF) range, i.e. between 100 kHz and 1 GHz and more specifically between 300-600 kHz. The RF electrical current is typically delivered from a generator via connected electrodes that are placed in a patient's body, in a region of tissue that contains a neural structure suspected of transmitting pain signals to the brain. The electrodes generally include an insulated shaft with an exposed conductive tip to deliver the radiofrequency electrical current. Tissue resistance to the current causes heating of tissue adjacent resulting in the coagulation of cells (at a temperature of approximately 45° C. for small unmyelinated nerve structures) and the formation of a lesion that effectively denervates the neural structure in question. Denervation refers to a procedure whereby the ability of a neural structure to transmit signals is affected in some way and usually results in the complete inability of a neural structure to transmit signals, thus removing the pain sensations. This procedure may be done in a monopolar mode where a second dispersive electrode with a large surface area is placed on the surface of a patient's body to complete the circuit, or in a bipolar mode where a second radiofrequency electrode is placed at the treatment site. In a bipolar procedure, the current is preferentially concentrated between the two electrodes.

To extend the size of a lesion, radiofrequency treatment may be applied in conjunction with a cooling mechanism, whereby a cooling means is used to reduce the temperature of the electrode-tissue interface, allowing a higher power to be applied without causing an unwanted increase in local tissue temperature that can result in tissue desiccation, charring, or steam formation. The application of a higher power allows regions of tissue further away from the energy delivery device to reach a temperature at which a lesion can form, thus increasing the size/volume of the lesion. The cooling means can include internal circulation of a cooling fluid fluid within a probe comprising the electrode, where the cooling fluid never contacts the patient, or through external irrigation, in which a physiologic solution is used to continuously irrigate and cool the electrode-tissue interface or treatment site. Regardless of the cooling approach, accurate control of the cooling fluid flow rate is critical in creating an effective lesion. However, known cooled radiofrequency treatment systems vary the speed of a pump that pumps the cooling fluid through the system to control the flow rate. Such an open loop approach is technically challenging and expensive to implement, particularly in configurations requiring high accuracy such irrigated cooling. Due to the inability in typical systems to directly measure the cooling fluid flow rate, open loop control must rely on high tolerance of the pump head and tubing, as well as consistent set up of the system to achieve repeatable speed based flow rate control.

The treatment of pain using high-frequency electrical current has been applied successfully to various regions of patients' bodies suspected of contributing to chronic pain sensations. For example, with respect to back pain, which affects millions of individuals every year, high-frequency electrical treatment has been applied to several tissues, including intervertebral discs, facet joints, sacroiliac joints as well as the vertebrae themselves (in a process known as intraosseous denervation). In addition to creating lesions in neural structures, application of radiofrequency energy has also been used to treat tumors throughout the body. Further, with respect to knee pain, which also affects millions of individuals every year, high-frequency electrical treatment has been applied to several tissues, including, for example, the ligaments, muscles, tendons, and menisci.

Thus, the art is continuously seeking new and improved systems and methods for treating chronic pain using cooled RF ablation techniques. For example, improved systems utilizing direct measure of a flow rate of a cooling fluid delivered to a distal end of a medical probe assembly would be useful. More particularly, systems having a flow sensor integrated in a tubing that provides cooling fluid to the medical probe assembly to directly measure the cooling fluid flow rate would be advantageous. Methods for controlling the cooling fluid flow rate using the closed-loop feedback control system enabled by the flow sensor also would be desirable.

SUMMARY

Objects and advantages of the invention will be set forth in part in the following description, or may be obvious from the description, or may be learned through practice of the invention.

In one aspect, the present subject matter is directed to a cooling system for a medical probe assembly. The cooling system comprises a pump assembly comprising a control unit having at least one controller, a motor, and a pump head driven by the motor. The cooling system further comprises a fluid reservoir, a lumen for delivering a cooling fluid to a distal end of the medical probe assembly, tubing for conveying the cooling fluid from the fluid reservoir to the lumen, and a flow sensor for sensing a flow rate of the cooling fluid. The tubing extends through the pump head, and the pump head is disposed between the fluid reservoir and the medical probe assembly to pump the cooling fluid from the fluid reservoir to the lumen through the tubing. The flow sensor is disposed between the pump head and the medical probe assembly to sense the flow rate of the cooling fluid. It should also be understood that the cooling system may further include any of the additional features as described herein.

In another aspect, the present disclosure is directed to a method for controlling a flow rate of fluid through a cooling circuit of a medical probe assembly. The method comprises pumping a cooling fluid through a tubing to a lumen for delivering a cooling fluid to a distal end of the medical probe assembly; sensing a flow rate of the cooling fluid; communicating a flow rate signal to a controller; processing the flow rate signal to produce a processed flow rate signal; and determining whether to adjust a motor speed to change the flow rate of the cooling fluid to the distal end of the medical probe assembly. It should also be appreciated that the method may further include any of the additional features as described herein.

In yet another aspect, the present disclosure is directed to a system for using a plurality of medical probe assemblies to deliver energy to a patient's body. The system comprises a plurality of cooling systems, and each cooling system is associated with one medical probe assembly of the plurality of medical probe assemblies. Each cooling system comprises a pump assembly including a control unit having at least one controller, a motor, and a pump head driven by the motor; a lumen for delivering a cooling fluid to a distal end of the medical probe assembly associated with the cooling system; tubing for conveying the cooling fluid from a fluid reservoir to the lumen, the tubing extending through the pump head; and a flow sensor for sensing a flow rate of the cooling fluid. The pump head is disposed between the fluid reservoir and the medical probe assembly associated with the cooling system to pump the cooling fluid from the fluid reservoir to the lumen through the tubing. The flow sensor is disposed between the pump head and the medical probe assembly associated with the cooling system to sense the flow rate of the cooling fluid. Further, each medical probe assembly of the plurality of medical probe assemblies comprises at least one probe having an elongate member with a distal region and a proximal region. The distal region comprises an electrically non-conductive outer circumferential portion. Each medical probe assembly also comprises an electrically and thermally-conductive energy delivery device extending distally from the electrically non-conductive outer circumferential portion for delivering one of electrical and radiofrequency energy to the patient's body. The energy delivery device comprises a conductive outer circumferential surface and an energy delivery device distal end that forms the distal end of the medical probe assembly to which the cooling fluid is delivered. It should also be understood that the cooling system may further include any of the additional features as described herein.

These and other features, aspects and advantages of the present subject matter will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present subject matter, including the best mode thereof, directed to one of ordinary skill in the art, is set forth in the specification, which makes reference to the appended figures, in which.

DETAILED DESCRIPTION

Reference will now be made in detail to one or more embodiments of the invention, examples of the invention, examples of which are illustrated in the drawings. Each example and embodiment is provided by way of explanation of the invention, and is not meant as a limitation of the invention. For example, features illustrated or described as part of one embodiment may be used with another embodiment to yield still a further embodiment. It is intended that the invention include these and other modifications and variations as coming within the scope and spirit of the invention.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

For the purposes of the present subject matter, a lesion refers to the region of tissue that has been irreversibly damaged as a result of the application of thermal energy, and the present subject matter is not intended to be limited in this regard. Further, for the purposes of this description, proximal generally indicates that portion of a device or system next to or nearer to a user (when the device is in use), while the term distal generally indicates a portion further away from the user (when the device is in use).

Generally, the present subject matter provides pump systems, pump assemblies, and pump heads for pumping fluid to one or more systems or assemblies. More particularly, the present subject matter provides a pump system comprising a plurality of pump assemblies, and each pump assembly of the plurality of pump assemblies supplies a fluid to a cooling circuit. The cooling circuit may be used to supply cooling fluid to the distal end of a medical probe assembly for delivering energy to a patient's body, e.g., as part of a treatment procedure. The pump system further comprises a base for supporting the plurality of pump assemblies. Each pump assembly described herein comprises a pump head, a bezel surrounding an outer perimeter of the pump head, a motor, and tubing.

In general, the pump head comprises an occlusion bed, a rotor guide, a rotor assembly positioned between the occlusion bed and the rotor guide, and a pathway for tubing. The tubing supplies fluid to the cooling circuit. The pathway comprises an inlet portion, an outlet portion, and a connecting portion that connects the inlet portion to the outlet portion. The inlet portion of the pathway is defined between the occlusion bed and the rotor guide, the outlet portion of the pathway is defined between the occlusion bed and the rotor guide, and the connecting portion of the pathway is defined between the occlusion bed and the rotor assembly.

Further, the occlusion bed is movable with respect to the rotor guide and the rotor assembly. As described herein, through such movement of the occlusion bed and other features, the pump head is configured to ease the task of inserting the tubing into the pump head such that correct insertion of the tubing is repeatable and safe. Once the tubing is inserted or loaded into the pump head, and the user is safely separated from the rotor assembly, e.g., by a rotor cover plate and pump head cover as described herein, the motor may be powered on to drive the rotor assembly and thereby begin pumping the fluid through the tubing.

Figure 1:
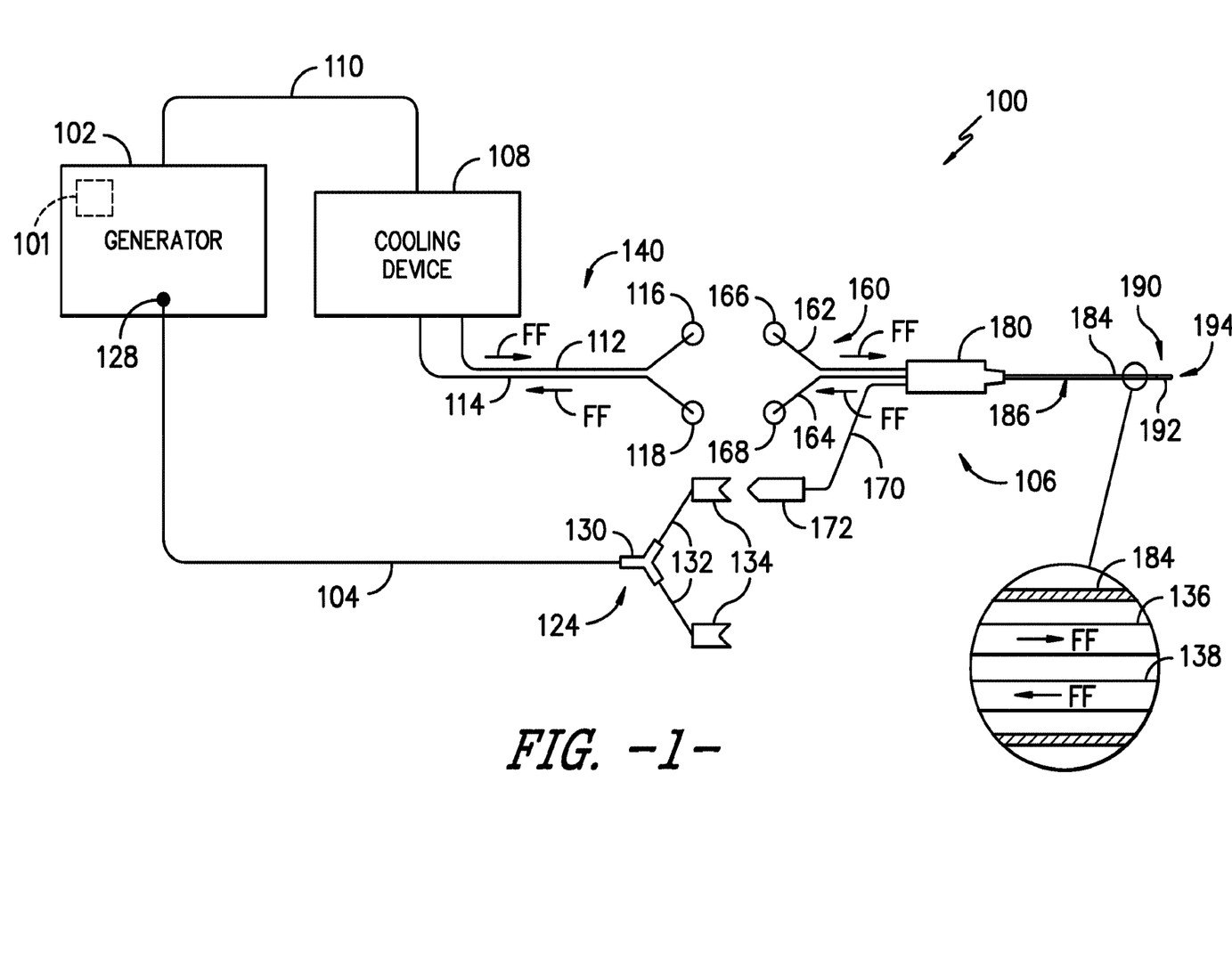
FIG. 1 provides a schematic illustration of a portion of a system for applying radiofrequency electrical energy to a patient's body according to an exemplary embodiment of the present subject matter.

Referring now to the drawings, FIG. 1 illustrates a schematic diagram of one embodiment of a system 100 of the present subject matter. As shown, the system 100 includes a generator 102; a cable 104; one or more probe assemblies 106 (only one probe assembly 106 is shown); one or more cooling devices 108; a pump cable 110; one or more proximal cooling supply tubes 112; and one or more proximal cooling return tubes 114. In an exemplary embodiment, the system 100 includes first, second, third, and fourth probe assemblies 106. As shown in the illustrated embodiment, the generator 102 is a radiofrequency (RF) generator, but optionally may be any power source that may deliver other forms of energy, including but not limited to microwave energy, thermal energy, ultrasound, and optical energy. Further, the generator 102 may include a display 103 (FIG. 2) incorporated therein. The display 103 may be operable to display various aspects of a treatment procedure, including but not limited to any parameters that are relevant to a treatment procedure, such as temperature, impedance, etc. and errors or warnings related to a treatment procedure. If no display 103 is incorporated into the generator 102, the generator 102 may include means of transmitting a signal to an external display. In one embodiment, the generator 102 is operable to communicate with one more devices, for example, with one or more of the probe assemblies 106 and the one or more cooling devices 108. Such communication may be unidirectional or bidirectional depending on the devices used and the procedure performed.

In addition, as shown, a distal region 124 of the cable 104 may include a splitter 130 that divides the cable 104 into two or more distal ends 132 such that the probe assemblies 106 can be connected thereto. A proximal end 128 of the cable 104 is connected to the generator 102. This connection can be permanent, whereby, for example, the proximal end 128 of the cable 104 is embedded within the generator 102, or temporary, whereby, for example, the proximal end 128 of cable 104 is connected to generator 102 via an electrical connector. The two or more distal ends 132 of the cable 104 terminate in connectors 134 operable to couple to the probe assemblies 106 and establish an electrical connection between the probe assemblies 106 and the generator 102. In alternate embodiments, the system 100 may include a separate cable for each probe assembly 106 being used to couple the probe assemblies 106 to the generator 102. Alternatively, the splitter 130 may include more than two distal ends. Such a connector is useful in embodiments having more than two devices connected to the generator 102, for example, if more than two probe assemblies are being used.

Figure 2:
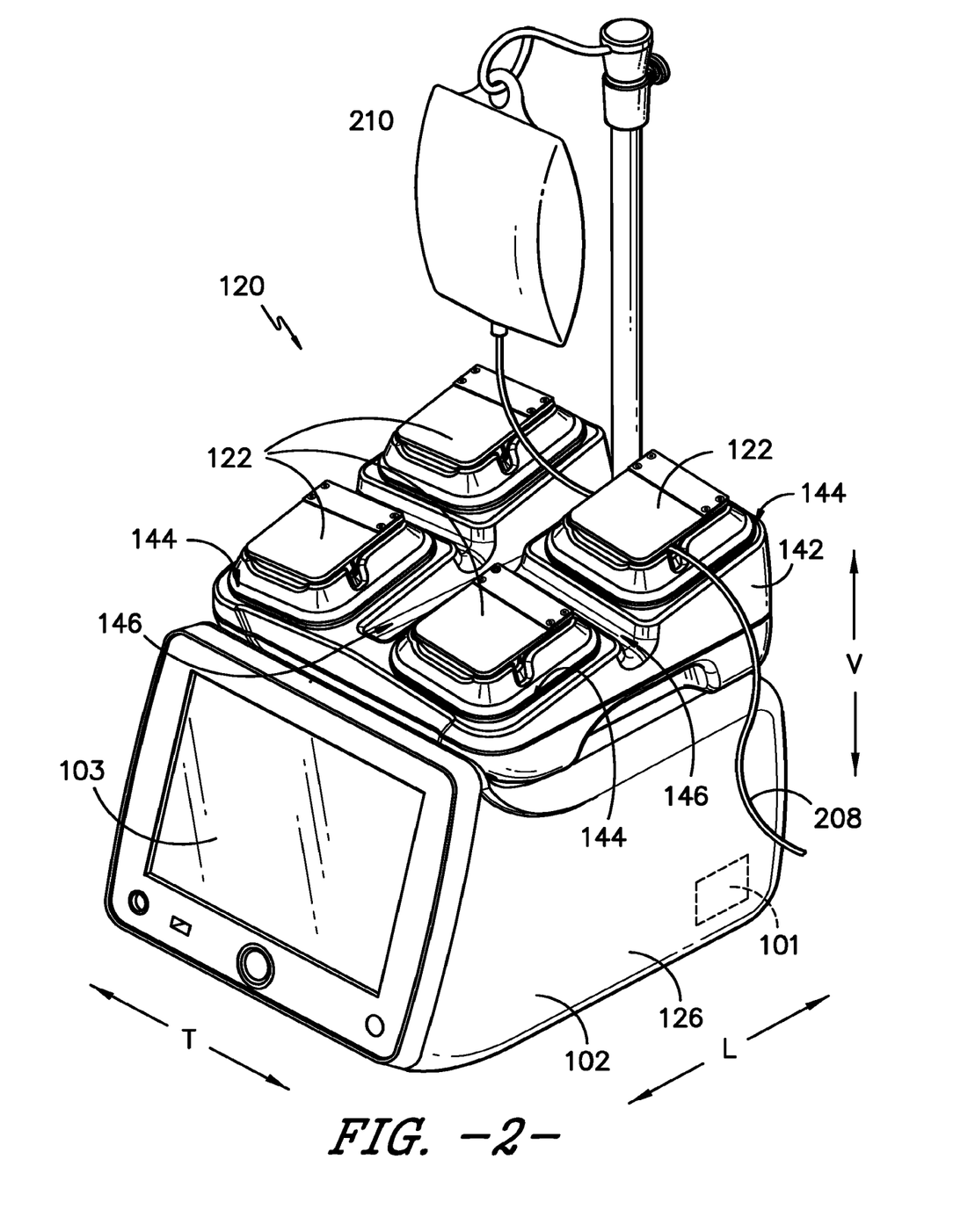
FIG. 2 provides a perspective view of the pump system of FIG. 1 according to an exemplary embodiment of the present subject matter.
Figure 3:
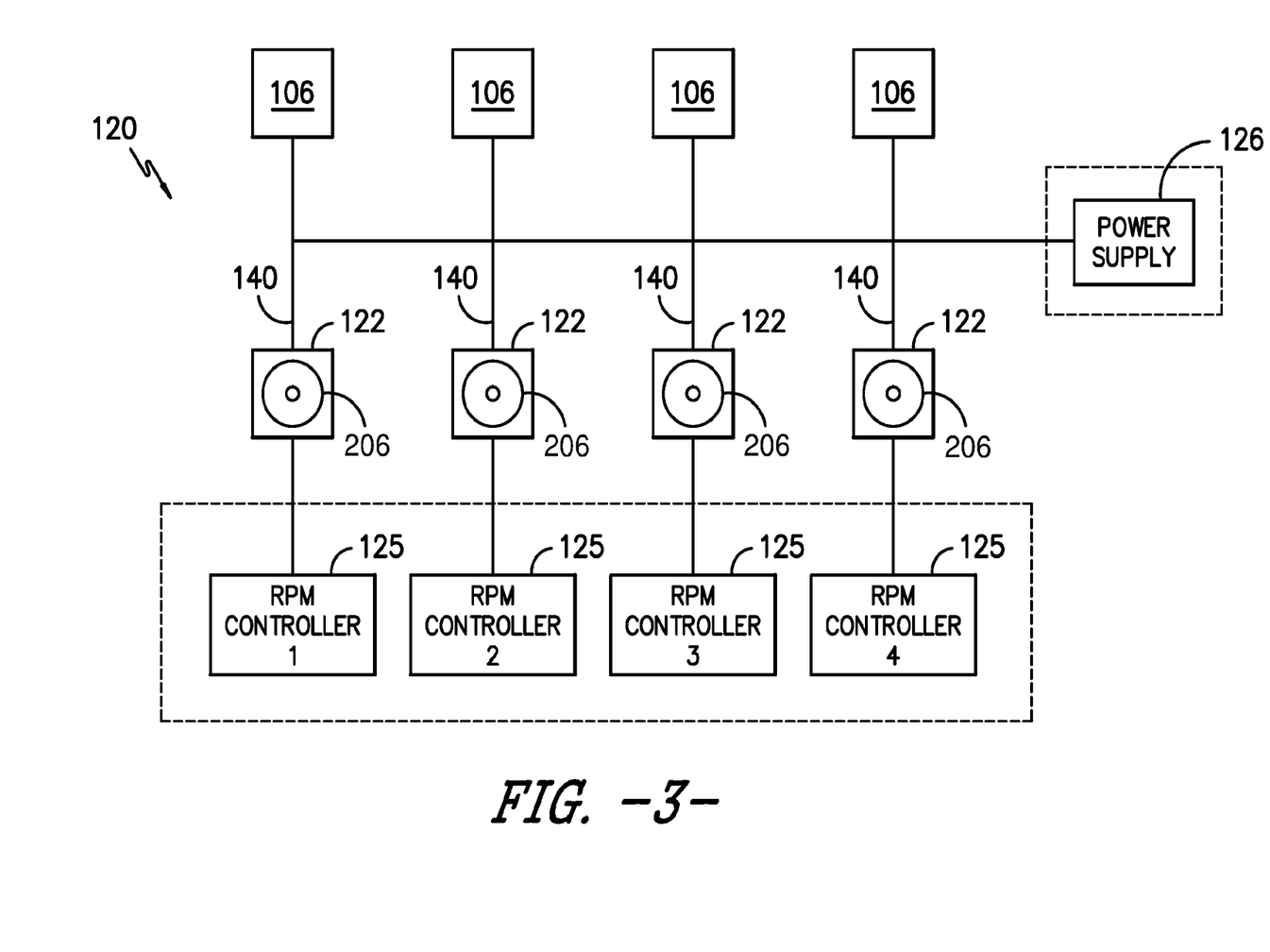
FIG. 3 provides a block diagram of the pump system of FIG. 1 according to an exemplary embodiment of the present subject matter.

The cooling device(s) 108 may include any means of reducing a temperature of material located at and proximate to one or more of the probe assemblies 106. For example, as shown in FIG. 2, the cooling devices 108 may include a pump system 120 having one or more peristaltic pump assemblies 122 operable to circulate a fluid from the cooling devices 108 through one or more proximal cooling supply tubes 112, the probe assemblies 106 (via internal lumens therein, as described in greater detail below), one or more proximal cooling return tubes 114 and back to the one or more cooling devices 108. For example, as shown in the illustrated embodiment of FIGS. 2 and 3, the pump system 120 includes four peristaltic pump assemblies 122 coupled to a power supply 126. In such embodiments, as shown in FIG. 3, each of the plurality of pump assemblies 122 may be in separate fluid communication with one of the probe assemblies. The fluid may be water or any other suitable fluid or gas. In alternate embodiments, the pump system 120 may include only one peristaltic pump assembly 122 or greater than four pump assemblies 122. In addition, as shown in FIG. 3, each of the pump assemblies 122 may have an independent speed (i.e., RPM) controller 125 that is configured to independently adjust the speed of its respective pump assembly. The pump system 120 and pump assemblies 122 are described in greater detail below.

Referring to FIG. 1, the system 100 may include a controller or control module 101 for facilitating communication between the cooling devices 108 and the generator 102. In this way, feedback control is established between the cooling devices 108 and the generator 102. The feedback control may include the generator 102, the probe assemblies 106, and the cooling devices 108, although any feedback between any two devices is within the scope of the present subject matter. The feedback control may be implemented, for example, in a control module that may be a component of the generator 102. In such embodiments, the generator 102 is operable to communicate bi-directionally with the probe assemblies 106 as well as with the cooling devices 108. In the context of the present subject matter, bi-directional communication refers to the capability of a device to both receive a signal from and send a signal to another device.

As an example, the generator 102 may receive temperature measurements from one or both of the first and second probe assemblies 106. Based on the temperature measurements, the generator 102 may perform some action, such as modulating the power that is sent to the probe assemblies 106. Thus, both probe assemblies 106 may be individually controlled based on their respective temperature measurements. For example, power to each of the probe assemblies 106 can be increased when a temperature measurement is low or can be decreased when a measurement is high. This variation of power may be different for each probe assembly. In some cases, the generator 102 may terminate power to one or more probe assemblies 106. Thus, the generator 102 may receive a signal (e.g., temperature measurement) from one or both of the first and second probe assemblies 106, determine the appropriate action, and send a signal (e.g., decreased or increased power) back to one or both of the probe assemblies 106. Alternatively, the generator 102 may send a signal to the cooling devices 108 to either increase or decrease the flow rate or degree of cooling being supplied to one or both of the first and second probe assemblies 106.

More specifically, the pump assemblies 122 may communicate a fluid flow rate to the generator 102 and may receive communications from the generator 102 instructing the pumps 122 to modulate this flow rate. In some instances, the peristaltic pump assemblies 122 may respond to the generator 102 by changing the flow rate or turning off for a period of time. With the cooling devices 108 turned off, any temperature sensing elements associated with the probe assemblies 106 would not be affected by the cooling fluid, allowing a more precise determination of the surrounding tissue temperature to be made. In addition, when using more than one probe assembly 106, the average temperature or a maximum temperature in the temperature sensing elements associated with the probe assemblies 106 may be used to modulate cooling.

In other embodiments, the cooling devices 108 may reduce the rate of cooling or disengage depending on the distance between the probe assemblies 106. For example, when the distance is small enough such that a sufficient current density exists in the region to achieve a desired temperature, little or no cooling may be required. In such an embodiment, energy is preferentially concentrated between first and second energy delivery devices 192 through a region of tissue to be treated, thereby creating a strip lesion. A strip lesion is characterized by an oblong volume of heated tissue that is formed when an active electrode is in close proximity to a return electrode of similar dimensions. This occurs because at a given power, the current density is preferentially concentrated between the electrodes and a rise in temperature results from current density. Thus, as illustrated by these examples, the controller 101 may actively control energy delivered to the tissue by controlling an amount of energy delivered through the energy delivery device(s) 192 and by controlling a flow rate through the pump assembly(ies) 122, e.g., the flow rate through tubing of a pump head 200 of a pump assembly 122.

The cooling devices 108 may also communicate with the generator 102 to alert the generator 102 to one or more possible errors and/or anomalies associated with the cooling devices 108. Such errors and/or anomalies may include whether cooling flow is impeded or if a lid of one or more of the cooling devices 108 is opened. The generator 102 may then act on the error signal by at least one of alerting a user, aborting the procedure, and modifying an action.

The controller 101, as well as the other controllers or microcontrollers described herein, such as the microcontroller 212 and motor controller 214, can include various components for performing various operations and functions. For example, the controller 101 can include one or more processor(s) and one or more memory device(s). The operation of the system 100, including the generator 102 and cooling device(s) 108, may be controlled by a processing device such as the controller 101, which may include a microprocessor or other device that is in operative communication with components of the system 100. In one embodiment, the processor executes programming instructions stored in memory and may be a general or special purpose processor or microprocessor operable to execute programming instructions, control code, or micro-control code. The memory may be a separate component from the processor or may be included onboard within the processor. Alternatively, the controller 101 may be constructed without using a processor or microprocessor, e.g., using a combination of discrete analog and/or digital logic circuitry (such as switches, amplifiers, integrators, comparators, flip-flops, AND gates, and the like) to perform control functionality instead of relying upon software. Components of the system 100 may be in communication with the controller 101 via one or more signal lines or shared communication busses.

Further, the one or more memory device(s) can store instructions that when executed by the one or more processor(s) cause the one or more processor(s) to perform the operations and functions, e.g., as those described herein for communicating a signal. In one embodiment, the generator 102 includes a control circuit having one or more processors and associated memory device(s) configured to perform a variety of computer-implemented functions (e.g., performing the methods, steps, calculations and the like disclosed herein). As used herein, the term "processor" refers not only to integrated circuits referred to in the art as being included in a computer, but also refers to a controller, a microcontroller, a microcomputer, a programmable logic controller (PLC), an application specific integrated circuit, and other programmable circuits. Additionally, the memory device(s) may generally comprise memory element(s) including, but not limited to, computer readable medium (e.g., random access memory (RAM)), computer readable non-volatile medium (e.g., a flash memory), a floppy disk, a compact disc-read only memory (CD-ROM), a magneto-optical disk (MOD), a digital versatile disc (DVD) and/or other suitable memory elements.

Such memory device(s) may generally be configured to store suitable computer-readable instructions that, when implemented by the controller(s) or processor(s) 101, configure the control circuit to perform various functions including, but not limited to, controlling an amount of energy delivered through the energy delivery device(s) 192, controlling a flow rate through the pump assembly(ies) 122, and/or other functions. More particularly, the instructions may configure the control circuit to perform functions such as receiving directly or indirectly signals from one or more sensors (e.g. voltage sensors, current sensors, and/or other sensors) indicative of various input conditions, and/or various other suitable computer-implemented functions, which enable the generator 102 or other components of system 100 to carry out the various functions described herein. An interface can include one or more circuits, terminals, pins, contacts, conductors, or other components for sending and receiving control signals. Moreover, the control circuit may include a sensor interface (e.g., one or more analog-to-digital converters) to permit signals transmitted from any sensors within the system to be converted into signals that can be understood and processed by the controller(s) or processor(s) 101.

Still referring to FIG. 1, the proximal cooling supply tubes 112 may include proximal supply tube connectors 116 at the distal ends of the one or more proximal cooling supply tubes 112. Additionally, the proximal cooling return tubes 114 may include proximal return tube connectors 118 at the distal ends of the one or more proximal cooling return tubes 114. In one embodiment, the proximal supply tube connectors 116 are female luer-lock type connectors and the proximal return tube connectors 118 are male luer-lock type connectors, although other connector types are intended to be within the scope of the present subject matter.

In addition, as shown in FIG. 1, the probe assembly 106 may include a proximal region 160, a handle 180, a hollow elongate shaft 184, and a distal tip region 190 that includes the one or more energy delivery devices 192. The elongate shaft 184 and the distal tip region 190 together form a probe 186 that contact a patient's body to deliver energy thereto. The hollow elongate shaft 184 also may be described as an outer circumferential portion 184 of the probe 186, and the energy delivery device 192 extends distally from the outer circumferential portion 184. As further described herein, the elongate shaft 184 may be an electrically non-conductive outer circumferential portion 184, e.g., the shaft 184 may be formed from an electrically non-conductive material or may be electrically insulated, and the energy delivery device(s) 192 may be electrically and thermally-conductive energy delivery device(s) 192.

The proximal region 160 includes a distal cooling supply tube 162, a distal supply tube connector 166, a distal cooling return tube 164, a distal return tube connector 168, a probe assembly cable 170, and a probe cable connector 172. In such embodiments, the distal cooling supply tube 162 and distal cooling return tube 164 are flexible to allow for greater maneuverability of the probe assemblies 106 but alternate embodiments with rigid tubes are possible. Further, in several embodiments, the distal supply tube connector 166 may be a male luer-lock type connector and the distal return tube connector 168 may be a female luer-lock type connector. Thus, the proximal supply tube connector 116 may be operable to interlock with the distal supply tube connector 166 and the proximal return tube connector 118 may be operable to interlock with the distal return tube connector 168.

The probe assembly 106 also may include a shaft supply tube 136 and a shaft return tube 138, which are internal lumens for circulating cooling fluid to a distal end of the probe assembly 106. The distal cooling supply tube 162 and the distal cooling return tube 164 may be connected to the shaft supply tube 136 and the shaft return tube 138, respectively, within the handle 180 of the probe assembly 106. In one embodiment, the shaft supply tube 136 and the shaft return tube 138 may be hypotubes made of a conductive material, such as stainless steel, that extend from the handle 180 through a lumen of the hollow elongate shaft 184 to distal tip region 190. The number of hypotubes used for supplying cooling fluid and the number used for returning cooling fluid and the combination thereof may vary and all such combinations are intended to be within the scope of the present invention. For example, in some embodiments, the cooling fluid may pass through the shaft supply tube 136 out of the probe assembly 106 to the treatment site in the patient's body, externally cooling the distal end 194 through irrigation of the treatment site. Thus, in such embodiments, the cooling fluid may be a physiologic solution suitable for contacting the patient, and the tubes used for returning the fluid to the fluid source may be omitted or unused.

As illustrated in FIG. 1, the cooling fluid flows in a cooling circuit 140 formed by the cooling device(s) 108, the distal tip region 190 of the probe, and the various supply and return tubes 112, 114, 162, 162, 136, 138. The arrows FF in FIG. 1 illustrate the direction of flow of the cooling fluid supplied by the cooling device(s) 108 through the cooling circuit 140. More specifically, the cooling fluid flows from the cooling device(s) 108, through proximal cooling supply tube 112 to distal cooling supply tube 162, through distal cooling supply tube 162 to shaft supply tube 136, through shaft supply tube 136 to the distal tip region 190, from the distal tip region 190 to shaft return tube 138, through shaft return tube 138 to distal return tube 164, through distal return tube 164 to proximal return tube 114, and through proximal return tube 114 to the cooling device(s) 108.

Referring still to FIG. 1, the probe cable connector 172 may be located at a proximal end of the probe assembly cable 170 and may be operable to reversibly couple to one of the connectors 134, thus establishing an electrical connection between the generator 102 and the probe assembly 106. The probe assembly cable 170 may include one or more conductors depending on the specific configuration of the probe assembly 106. For example, in one embodiment, the probe assembly cable 170 may include five conductors allowing probe assembly cable 170 to transmit RF current from the generator 102 to the one or more energy delivery devices 192, as well as to connect multiple temperature sensing elements to the generator 102.

In addition, the handle 180 may be operable to easily and securely couple to an optional introducer tube, e.g., in an embodiment where an introducer tube would facilitate insertion of the one or more probe assemblies 106 into a patient's body. For instance, as shown, the handle 180 may taper at its distal end to accomplish this function, i.e., to enable the handle 180 to securely couple to an optional introducer tube. Generally, introducer tubes may include a proximal end, a distal end, and a longitudinal bore extending therebetween. Thus, the introducer tubes (when used) are operable to easily and securely couple with the probe assembly 106. For example, the proximal end of the introducer tubes may be fitted with a connector able to mate reversibly with the handle 180 of a probe assembly 106. An introducer tube may be used to gain access to a treatment site within a patient's body, and the hollow elongate shaft 184 of a probe assembly 106 may be introduced to the treatment site through the longitudinal bore of the introducer tube. Introducer tubes may further include one or more depth markers to enable a user to determine the depth of the distal end of the introducer tube within a patient's body. Additionally, introducer tubes may include one or more radiopaque markers to ensure the correct placement of the introducers when using fluoroscopic guidance.

The introducer tubes may be made of various materials, as is known in the art and, if the material is electrically conductive, the introducer tubes may be electrically insulated along all or part of their length, to prevent energy from being conducted to undesirable locations within a patient's body. In some embodiments, the elongate shaft 184 may be electrically conductive, and an introducer may function to insulate the shaft 184, leaving the energy delivery device 192 exposed for treatment. Further, the introducer tubes may be operable to connect to a power source and, therefore, may form part of an electrical current impedance monitor (wherein at least a portion of the introducer tube is not electrically insulated). Different tissues may have different electrical impedance characteristics, and therefore, it is possible to determine tissue type based on impedance measurements, as has been described. Thus, it would be beneficial to have a means of measuring impedance to determine the type of tissue within which a device is located. In addition, the gauge of the introducer tubes may vary depending on the procedure being performed and/or the tissue being treated. In some embodiments, the introducer tubes should be sufficiently sized in the radial dimension so as to accept at least one probe assembly 106. Moreover, in alternative embodiments, the elongate shaft 184 may be insulated so as not to conduct energy to portions of a patient's body that are not being treated.

The system 100 also may include one or more stylets. A stylet may have a beveled tip to facilitate insertion of the one or more introducer tubes into a patient's body. Various forms of stylets are well known in the art and the present subject matter is not limited to include only one specific form. Further, as described above with respect to the introducer tubes, the stylets may be operable to connect to a power source and may therefore form part of an electrical current impedance monitor. In other embodiments, one or more of the probe assemblies 106 may form part of an electrical current impedance monitor. Thus, the generator 102 may receive impedance measurements from one or more of the stylets, the introducer tubes, and/or the probe assemblies 106 and may perform an action, such as alerting a user to an incorrect placement of an energy delivery device 192, based on the impedance measurements.

The energy delivery devices 192 may include any means of delivering energy to a region of tissue adjacent to the distal tip region 190. For example, the energy delivery devices 192 may include an ultrasonic device, an electrode, or any other energy delivery means, and the present subject matter is not limited in this regard. Similarly, energy delivered via the energy delivery devices 192 may take several forms, including but not limited to thermal energy, ultrasonic energy, radiofrequency energy, microwave energy, or any other form of energy. For example, in one embodiment, the energy delivery devices 192 may include an electrode. The active region of the electrode 192 may be 2 to 20 millimeters (mm) in length and energy delivered by the electrode is electrical energy in the form of current in the RF range. The size of the active region of the electrode can be optimized for placement within, e.g., an intervertebral disc; however, different sizes of active regions, all of which are within the scope of the present subject matter, may be used depending on the specific procedure being performed. In some embodiments, feedback from the generator 102 may automatically adjust the exposed area of the energy delivery device 192 in response to a given measurement, such as impedance or temperature. For example, in one embodiment, the energy delivery devices 192 may maximize energy delivered to the tissue by implementing at least one additional feedback control, such as a rising impedance value. As previously described, each energy delivery device 192 may be electrically and thermally-conductive and may comprise a conductive outer circumferential surface to conduct electrical energy and heat from the distal tip region 190 of the probe 186 to a patient's body. Further, the distal tip region 190 includes one or more temperature sensing elements, which are operable to measure the temperature at and proximate to the one or more energy delivery devices 192. The temperature sensing elements may include one or more thermocouples, thermometers, thermistors, optical fluorescent sensors or any other means of sensing temperature.

In one embodiment, the first and second probe assemblies 106 may be operated in a bipolar mode. For example, the distal tip region 190 of each of two probe assemblies may be located within an intervertebral disc. In such embodiments, electrical energy is delivered to the first and second probe assemblies 106, and this energy is preferentially concentrated therebetween through a region of tissue to be treated (i.e., an area of the intervertebral disc). The region of tissue to be treated is thus heated by the energy concentrated between the first and second probe assemblies 106. In other embodiments, the first and second probe assemblies 106 may be operated in a monopolar mode, in which case an additional grounding pad is required on the surface of a body of a patient, as is known in the art. Any combination of bipolar and monopolar procedures may also be used. It should also be understood that the system may include more than two probe assemblies 100. For example, in some embodiments, three probe assemblies 106 may be used, and the probe assemblies 106 may be operated in a triphasic mode, whereby the phase of the current being supplied differs for each probe assembly 106. In further embodiments, the system 100 may be configured to control one or more of the flow of current between electrically conductive components and the current density around a particular component. In such embodiments, the system 100 may be configured to alternate between monopolar configurations, bipolar configurations, or quasi-bipolar configurations during a treatment procedure.

As a particular example, to treat tissue of a patient's body according to an exemplary embodiment of the present subject matter, the energy delivery device 192 of each of two probe assemblies 106 may be inserted into the patient's body, e.g., using an introducer and stylet as described herein. Once a power source, such as the generator 102, is connected to the probe assemblies 106, a stimulating electrical signal may be emitted from either of the electrodes 192 to a dispersive electrode or to the other electrode 192. This signal may be used to stimulate sensory nerves, where replication of symptomatic pain would verify that the tissue, such as an intervertebral disc, is pain-causing. Simultaneously, the cooling fluid may be circulated through the internal lumens 136, 138 of the probe assemblies 106 via the pump assemblies 122 and energy may be delivered from the RF generator 102 to the tissue through the energy delivery devices 192. In other words, radiofrequency energy is delivered to the electrodes 192 and the power is altered according to the temperature measured by the temperature sensing element in the tip of the electrodes 192 such that a desired temperature is reached between the distal tip regions 190 of the two probe assemblies 106. During the procedure, a treatment protocol such as the cooling supplied to the probe assemblies 106 and/or the power transmitted to the probe assemblies 106 may be adjusted and/or controlled to maintain a desirable treatment area shape, size and uniformity. More specifically, actively controlling energy delivered to the tissue by controlling both an amount of energy delivered through the energy delivery devices 192 and individually controlling the flow rate of the pump assemblies 122. In further embodiments, the generator 102 may control the energy delivered to the tissue based on the temperature measured by the temperature sensing element(s) in the distal tip region 190 of the probe assemblies 106 and/or based on impedance sensors.

Figure 4:
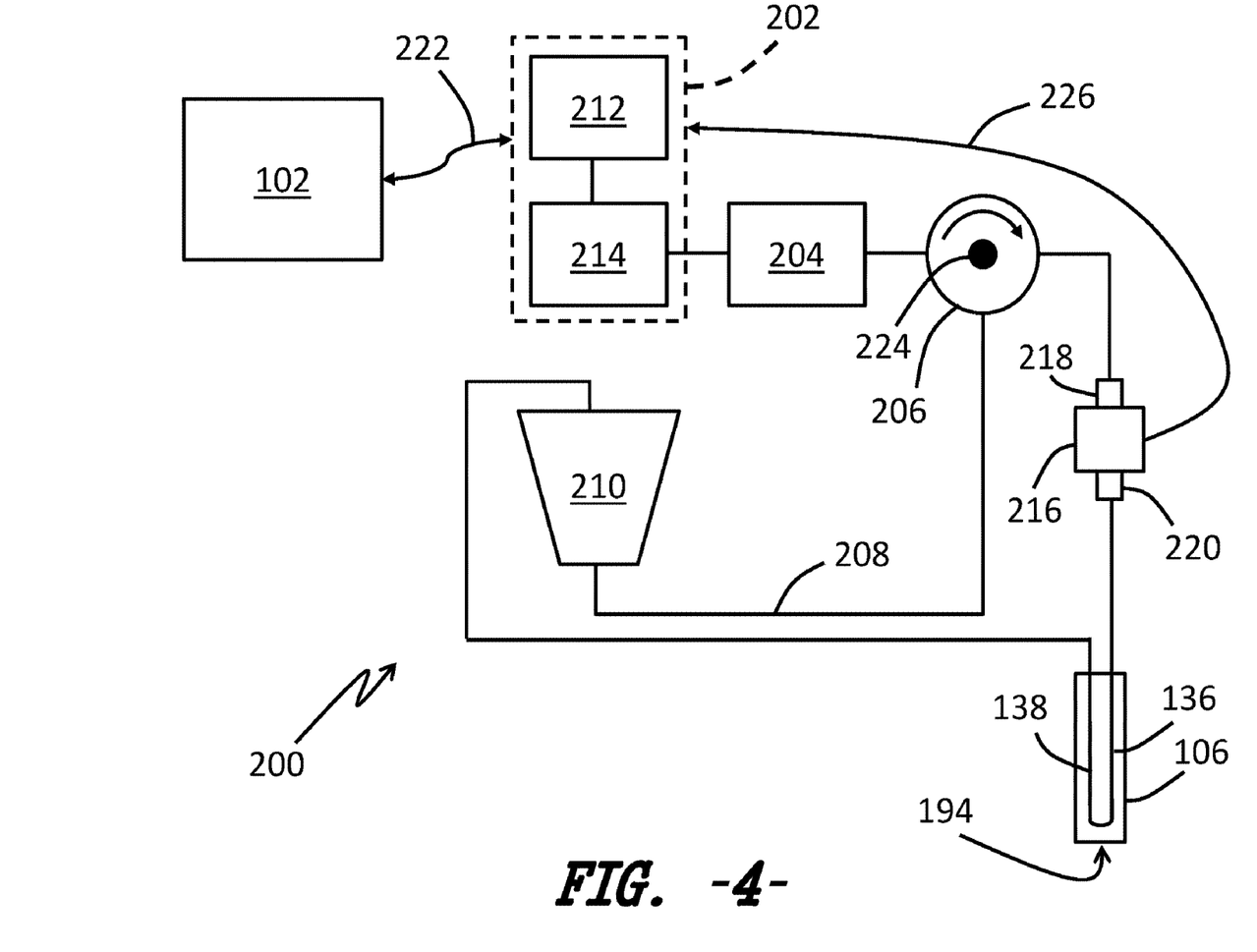
FIG. 4 provides a schematic diagram illustrating a cooling system for a medical probe assembly of FIG. 1.

Referring now to FIG. 4, a schematic diagram is provided illustrating a cooling system 200 for the medical probe assembly 106, according to an exemplary embodiment of the present subject matter. As shown in FIG. 4, the cooling system 200 includes the cooling circuit 140 described in greater detail herein. More particularly, the cooling system 200 includes one or more pump assemblies 122, and each pump assembly 122 supplies a cooling fluid to a probe assembly 106 via the cooling circuit 140, which provides a pathway for the cooling fluid from a fluid source or reservoir 210 to the distal end 194 of the probe assembly 106. In some embodiments, as described herein, the cooling circuit 140 includes a cooling device 108 and its associated cooling supply tube and connector 112, 116 and cooling return tube and connector 114, 118, as well as the cooling supply tube and connector 162, 166, cooling return tube and connector 164, 168, and internal lumens (i.e., shaft supply and return tubes) 136, 138 of the probe assembly 106. In other embodiments, such as those embodiments in which the distal end 194 of the probe assembly 106 is cooled by external irrigation of the treatment site, the cooling return tube and connector 114, 118, cooling return tube and connector 164, 168, and lumen or return tube 138 may be omitted.

As illustrated in FIG. 4, the pump assembly 122 comprises a control unit 202 having at least one controller, a motor 204, and a pump head 206 driven by the motor 204. The motor 204 is directly coupled to the pump head 206 to drive the fluid pumping mechanism, and the pump head 206 has a rotor assembly 224 that may rotate clockwise (as shown in FIG. 4) or counterclockwise. The cooling system 200 further comprises a tubing 208 and a fluid reservoir 210, which also are illustrated in FIG. 2 and are part of the cooling circuit 140. In exemplary embodiments, the pump assembly 122 is a peristaltic pump assembly. As such, the tubing 208 extends through the pump head 206, and the pump head 206, driven by the motor 204, compresses the tubing 208 to draw a cooling fluid from the fluid reservoir 210 and pump the cooling fluid into a lumen 136 that delivers the cooling fluid to the distal end 194 of the energy delivery device 192, as previously described. Thus, the tubing 208 conveys the cooling fluid from the fluid reservoir 210 to the lumen 136 (also referred to herein as the shaft supply tube 136). In some embodiments, the lumen 136 is disposed within the probe assembly 106 such that the cooling fluid circulates within the probe assembly 106, e.g., within the shaft 184 at or near the distal end 194. In other embodiments, the lumen 136 is disposed within the probe assembly 106 such that the cooling fluid exits the probe assembly 106 at the distal end 194, e.g., to irrigate a treatment site of the probe assembly 106.

In the exemplary embodiment depicted in FIG. 4, the control unit 202 comprises two controllers, microcontroller 212 and motor controller 214. It will be appreciated that, in some embodiments, the microcontroller 212 and motor controller 214 may be separate control or processor modules. Alternatively, the functions described with respect to the microcontroller 212 and the functions described with respect to the motor controller 214 may be performed by a single controller or module.

As shown in the figures, the cooling system 200 further comprises a flow sensor 216 for sensing a flow rate of the cooling fluid through the cooling system 200. More particularly, the pump head 206 is disposed between the fluid reservoir 210 and the probe assembly 106 to pump the cooling fluid from the fluid reservoir 210 to the lumen 136 through the tubing 208. The flow sensor 216 is disposed between the pump head 206 and the probe assembly 106, in fluid communication with the flow of cooling fluid, to sense the flow rate of the cooling fluid. In some embodiments, the flow sensor 216 is positioned in the tubing 208 to detect the flow rate of the cooling fluid through the tubing 208 upstream of the probe assembly 106, but in other embodiments, the flow sensor 216 is positioned in the lumen 136 to detect the flow rate of the cooling fluid through the lumen 136 upstream of the probe assembly distal end 194.

In the exemplary embodiment depicted in FIG. 4, the flow sensor 216 comprises an inlet port 218 for an ingress of the cooling fluid into the flow sensor 216 and an outlet port 220 for an egress of the cooling fluid from the flow sensor 216. More specifically, the inlet port 218 and the outlet port 220 of the flow sensor 216 are connected inline to the tubing 208, such that the cooling fluid flows through the flow sensor 216. As such, the flow sensor 216 may include a wetted surface that is made from an inert, biocompatible material. The inline connection of the inlet and outlet ports 218, 220 with the tubing 208 may be established during manufacturing of the tubing 208, i.e., the flow sensor 216 may be installed in the tubing 208 during its manufacture. In some embodiments, the flow sensor 216 is sterilizable, such that it may be sterilized after use in a single procedure and then re-used in another procedure, but in other embodiments, the flow sensor 216 is configured for single, one-time use and may be disposed of after use in a single procedure. Further, the flow sensor 216 may be a mass flow sensor and/or may be an ultrasonic flow sensor.

As will be described in greater detail with respect to FIG. 5, the flow sensor 216 outputs a flow rate signal to the control unit 202, which includes at least one controller 212, 214. As illustrated in FIG. 4, a communication pathway 226, such as a unidirectional communication pathway from the flow sensor 216 to the microcontroller 212, may be maintained between the flow sensor 216 and the control unit 202. The control unit 202 is configured to process the flow rate signal to obtain a processed flow rate signal. The control unit 202 outputs the processed flow rate signal to the generator 102, which may be a radiofrequency generator or other power source for the energy delivery device 192 as described herein, for determining whether to adjust a speed of the motor 204. That is, the generator 102 outputs parameters or data, including pumping speed, rotational direction, motor acceleration, and motor deceleration, to the control unit 202, which maintains a bi-directional communication pathway 222 with the generator 102. The control unit 202, in turn, interprets the parameters or data from the generator 102 and, via the motor controller 214, modulates the motor speed to thereby control the speed of the pump head 206, e.g., by modulating the power supplied to the motor 204 to control the rotation of the motor 204, which controls the rotational speed of a rotor assembly 224 of the pump head 206. Thus, based on the input to the motor 204 from the generator 102, the pump head 206 rotor assembly speed is modulated to adjust the flow rate of the cooling fluid delivered to the distal end 194 of the probe assembly 106. That is, the tubing 208 extending through the pump head 206 is acted on by the pump head rotor assembly 224 to pump the cooling fluid through the cooling circuit 140 and to the distal end 194 (either internally within the probe assembly 106 or externally at the treatment site). Accordingly, varying the rotational speed of the rotor assembly 224, which is controlled by the motor 204, varies the flow rate of the cooling fluid through the tubing 208 and the lumen 136.

Figure 5:
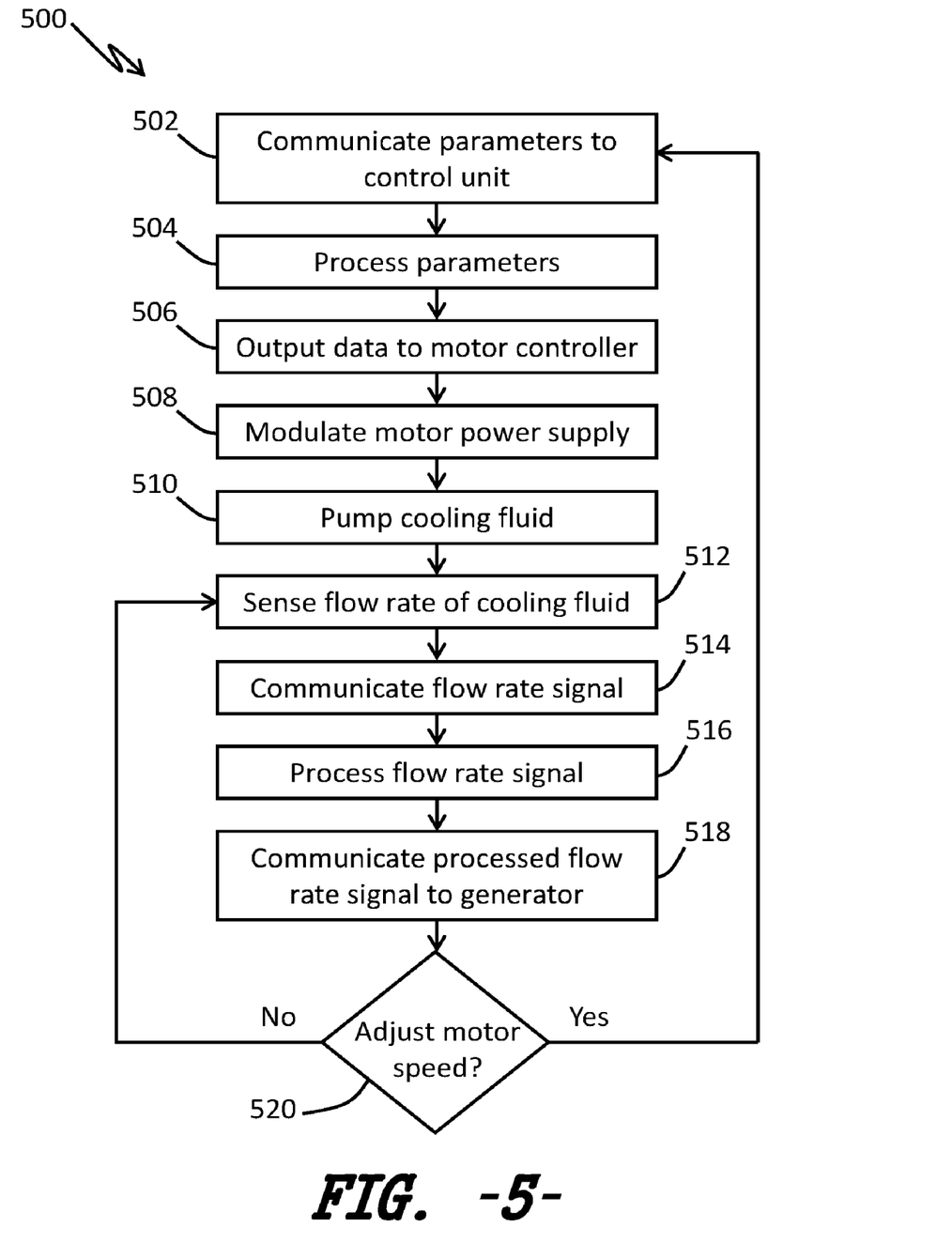
FIG. 5 provides a flow diagram illustrating a method for controlling a flow rate of fluid through a cooling circuit of a medical probe assembly, according to an exemplary embodiment of the present subject matter.

Referring now to FIG. 5, methods for controlling a flow rate of fluid through a cooling circuit of a medical probe assembly will be described, according to exemplary embodiments of the present subject matter. As shown at 502, the exemplary method 500 includes communicating parameters such as pumping speed, rotational direction, motor acceleration, and motor deceleration to the control unit 202. As previously described, the generator 102 includes a controller or control module 101 that controls various aspects of a procedure performed using one or more probe assemblies 106 of the system 100. The generator controller 101 thus determines the cooling flow needed for the particular procedure, and communicates the relevant parameters to the control unit 202 to achieve the needed flow rate of the cooling fluid. In exemplary embodiments, the generator 102 communicates the parameters to the microcontroller 212 over the communication pathway 222. As shown at 504 and 506 of FIG. 5, the microcontroller 212, or other appropriate controller or control module of the control unit 202, interprets or processes the parameters from the generator 102 and outputs a motor speed signal to the motor controller 214, or other suitable controller or control module of the control unit 202. As illustrated at 508, the motor controller 214 then modulates the motor power supply to control the motor rotational speed based on the motor speed signal, i.e., the input parameter to the motor controller 214 derived from the output parameters from the generator 102. The motor 204, which is directly coupled to the rotor assembly 224 of the pump head 206, determines the pumping action by the pump head 206. Thus, once the motor 204 is activated at a given rotational speed, the cooling system 200 begins pumping the cooling fluid from the fluid reservoir 210 through the tubing 208 to the 136 lumen to deliver the cooling fluid to the distal end 194 of the probe assembly 106, as shown at 510 of FIG. 5.

As depicted at 512, the method 500 includes sensing the flow rate of the cooling fluid, i.e., using the flow sensor 216 disposed between the pump head 206 and the probe assembly 106 as described herein. That is, as the cooling fluid flows through the cooling circuit 140, the flow sensor 216, which may be installed inline in either the tubing 208 or lumen 136 such that the cooling fluid enters through the inlet port 218 and exits through the outlet port 220, receives the flow of cooling fluid and determines its flow rate. As shown at 514, the flow sensor 216 communicates a flow rate signal to the control unit 202, e.g., over the communication pathway 226. As such, the flow sensor 216 measures the flow rate of the cooling fluid and outputs the flow data to the control unit 202, e.g., to the microcontroller 212, as an analog or digital flow rate signal. The control unit 202, e.g., the microcontroller 212, processes the flow rate signal to produce a processed flow rate signal, as shown at 516 in method 500. For example, the microcontroller 212 applies signal processing techniques in real time and outputs the processed signal to the generator 102. The control unit 202 then communicates the processed flow rate signal to the generator 102, e.g., over the communication pathway 222, as shown at 518 in method 500.

Depending on the power and other ablation or treatment requirements, the generator 102 can use the processed flow rate signal to then control the rotational parameters of the pump assembly 122 in real-time, e.g., to optimize the treatment procedure. More particularly, as shown at 520 in FIG. 5, the generator 102 determines whether to adjust the speed of the motor 204 based on the processed flow rate signal that has been communicated to the generator 102 and the desired or optimal parameters of the treatment procedure, i.e., whether a different flow rate of the cooling fluid is needed to achieve a desired effect. If the generator 102 determines the motor speed (and thus the flow rate) should be adjusted, the method 500 returns to 502 of method 500, where the generator 102 communicates a motor speed signal to the control unit 202, e.g., to the microcontroller 212, which processes the motor speed signal as shown at 504. The microcontroller 212 outputs the processed data to the motor controller 214 as illustrated at 506, which modulates the motor power supply and, thus, the rotational speed of the pump head rotor assembly 224 to adjust or change the flow rate of the cooling fluid pumped through the cooling circuit 140 to the distal end 194 of the probe assembly 106, as shown at 508. However, if the generator 102 determines the motor speed and cooling fluid flow rate should not be adjusted, the flow sensor 216 continues sensing the flow rate as depicted at 512, and the flow rate data is continually communicated to the generator 102 such that the flow rate may be adjusted when appropriate or desired, e.g., based on the operational parameters of the treatment procedure.

Although described herein as including a control unit 202 that performs particular functions, it will be appreciated that, in some embodiments, the control unit 202 may be omitted and its functions may be performed by, e.g., the controller 101 of the generator 102. That is, the microcontroller module 212 and motor controller module 214 may be part of the generator 102 rather than a separate control unit 202. Further, although described herein only with respect to a single pump assembly 122 and probe assembly 106, it will be understood that the present subject matter may be applied to more than one pump assembly 122 and probe assembly 106 of the system 100. More particularly, where the system 100 includes more than one probe assembly 106 and associated pump assembly 122 for providing cooling fluid to the distal end 194 of the probe assembly 106, each probe assembly 106 or a portion of the probe assemblies 106 may include a cooling system 200 as described herein. Each cooling system 200 may operate independently to provide a cooling fluid flow rate required for its associated probe assembly 106, i.e., the flow rate of cooling fluid provided to each probe assembly 106 may be different or the same, based on the needs or requirements of the treatment procedure.

Accordingly, the present subject matter provides cooling systems for providing cooling fluid to medical probe assemblies and methods for controlling a flow rate of cooling fluid to a medical probe assembly. As described herein, the cooling systems and methods utilize a flow sensor installed in a cooling circuit through which the cooling fluid flows to measure or sense the flow rate of the cooling fluid through the cooling circuit. The flow sensor communicates the flow data to one or more controllers or processors, which process the flow data and determine whether the speed of a motor, which controls the rotor assembly of a pump head, should be modulated or adjusted to change the flow rate of the cooling fluid through the cooling circuit. That is, the motor speed determines the pumping speed of the associated pump, which determines the flow rate of the cooling fluid through the tubing extending through the pump. Therefore, the methods and systems described herein utilize a direct measure, closed loop feedback approach for determining and controlling the flow rate of cooling fluid to a medical probe assembly. Such a direct measure approach is more accurate than other indirect or open loop non-feedback approaches for controlling the fluid flow rate, such as using only the rotational speed of the pump to control the flow rate. The indirect or open loop systems require high tolerance pumps and components that are capable of repeatedly being accurately set up. Therefore, the direct measure or closed loop approach can reduce the costs of the system, e.g., by utilizing cheaper pumps because high pump tolerances are not required. Of course, as described herein, other advantages and benefits in addition to more accurate flow rate control and reduced system costs may be realized from the present subject matter.

A system of the present subject matter may be used in various medical procedures where usage of an energy delivery device may prove beneficial. Specifically, the system of the present subject matter is particularly useful for procedures involving treatment of back pain, including but not limited to treatments of tumors, intervertebral discs, facet joint denervation, sacroiliac joint lesioning or intraosseous (within the bone) treatment procedures. Moreover, the system is particularly useful to strengthen the annulus fibrosus, shrink annular fissures and impede them from progressing, cauterize granulation tissue in annular fissures, and denature pain-causing enzymes in nucleus pulposus tissue that has migrated to annular fissures. Additionally, the system may be operated to treat a herniated or internally disrupted disc with a minimally invasive technique that delivers sufficient energy to the annulus fibrosus to breakdown or cause a change in function of selective nerve structures in the intervertebral disc, modify collagen fibrils with predictable accuracy, treat endplates of a disc, and accurately reduce the volume of intervertebral disc tissue. The system is also useful to coagulate blood vessels and increase the production of heat shock proteins.

Using liquid-cooled probe assemblies 106 with an appropriate feedback control system as described herein also contributes to the uniformity of the treatment. The cooling distal tip regions 190 of the probe assemblies 106 helps to prevent excessively high temperatures in these regions which may lead to tissue adhering to the probe assemblies 106 as well as an increase in the impedance of tissue surrounding the distal tip regions 190 of the probe assemblies 106. Thus, by cooling the distal tip regions 190 of the probe assemblies 106, higher power can be delivered to tissue with a minimal risk of tissue charring at or immediately surrounding the distal tip regions 190. Delivering higher power to energy delivery devices 192 allows tissue further away from the energy delivery devices 192 to reach a temperature high enough to create a lesion and thus the lesion will not be limited to a region of tissue immediately surrounding the energy delivery devices 192 but will rather extend preferentially from a distal tip region 190 of one probe assembly 106 to the other.

As has been mentioned, a system of the present subject matter may be used to produce a relatively uniform lesion substantially between two probe assemblies 106 when operated in a bipolar mode. Oftentimes, uniform lesions may be contraindicated, such as in a case where a tissue to be treated is located closer to one energy delivery device 192 than to the other. In cases where a uniform lesion may be undesirable, using two or more cooled probe assemblies 106 in combination with a suitable feedback and control system may allow for the creation of lesions of varying size and shape. For example, preset temperature and/or power profiles that the procedure should follow may be programmed into the generator 102 prior to commencement of a treatment procedure. These profiles may define parameters (these parameters would depend on certain tissue parameters, such as heat capacity, etc.) that should be used to create a lesion of a specific size and shape. These parameters may include, but are not limited to, maximum allowable temperature, ramp rate (i.e. how quickly the temperature is raised) and the rate of cooling flow, for each individual probe. Based on temperature or impedance measurements performed during the procedure, various parameters, such as power or cooling, may be modulated, to comply with the preset profiles, resulting in a lesion with the desired dimensions.

Similarly, it is to be understood that a uniform lesion can be created, using a system of the present subject matter, using many different pre-set temperature and/or power profiles which allow the thermal dose across the tissue to be as uniform as possible, and that the present subject matter is not limited in this regard.

It should be noted that the term radiopaque marker as used herein denotes any addition or reduction of material that increases or reduces the radiopacity of the device. Further, the terms probe assembly, introducer, stylet etc. are not intended to be limiting and denote any medical and surgical tools that can be used to perform similar functions to those described. In addition, the subject matter is not limited to be used in the clinical applications disclosed herein, and other medical and surgical procedures wherein a device of the present subject matter would be useful are included within the scope of the present subject matter.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the present subject matter has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims or if they include equivalent structural elements with insubstantial differences from the literal language of the claims.

What is claimed is:

1. A cooling system for a medical probe assembly, the cooling system comprising:
    a pump assembly comprising a first controller configured to control at least one of a speed or a direction of rotation for a motor;
    a first lumen for delivering a cooling fluid to a distal end of the medical probe assembly;
    a sensor for sensing a flow rate of the cooling fluid, the sensor interrupting the first lumen and disposed between the pump assembly and the medical probe assembly and
    a radiofrequency (RF) generator comprising a second controller in communication with the first controller, the second controller configured to:
    store a set of parameters for a treatment procedure;
    receive an indication of the flow rate of the cooling fluid from the first controller;
    determine whether to adjust one of the speed or the direction of rotation for the motor based on the indicated flow rate and the set of parameters; and
    transmit a control signal to the first controller responsive to a determination to adjust one of the speed or the direction of rotation, the control signal causing the first controller to control the motor to adjust the speed or the direction of rotation accordingly.

2. The cooling system of claim 1, wherein the sensor is a flow sensor comprising an inlet port for an ingress of the cooling fluid and an outlet port for an egress of the cooling fluid.

3. The cooling system of claim 2, wherein the inlet port and the outlet port are connected inline with the first lumen.

4. The cooling system of claim 2, wherein the flow sensor comprises a wetted surface that is made from an inert, biocompatible material.

5. The cooling system of claim 1, wherein the flow sensor outputs a flow rate signal to the first controller.

6. The cooling system of claim 5, wherein the at least one controller is configured to process the flow rate signal to determine the flow rate.

7. The cooling system of claim 1, wherein the first lumen is disposed within the medical probe assembly such that the cooling fluid circulates within the medical probe assembly.

8. The cooling system of claim 1, wherein the first lumen is disposed within the medical probe assembly such that the cooling fluid exits the medical probe assembly at the distal end to irrigate a treatment site of the medical probe assembly.

9. The cooling system of claim 1, wherein the first controller is at least one of a microcontroller or a motor controller.

10. The cooling system of claim 1, wherein the pump assembly comprises a peristaltic pump.

11. The cooling system of claim 1, wherein the medical probe assembly comprises a probe having an energy delivery device for delivering energy to a patient's body positioned at the distal end.

* * * * *